United States Patent [19]

Cardillo et al.

[11] Patent Number: 5,168,054

[45] Date of Patent: Dec. 1, 1992

[54] PROCESS FOR THE MICROBIOLOGICAL PRODUCTION OF GAMMA- AND DELTA-LACTONES

[75] Inventors: Rosanna Cardillo; Claudio Fuganti, both of Milan; Massimo Barbeni; Paolo Cabella, both of Turin; Pier A. Guarda, Druento Torino; Gianna Allegrone, Turin, all of Italy

[73] Assignee: Pernod-Ricard, Paris, France

[21] Appl. No.: 563,036

[22] Filed: Aug. 6, 1990

[30] Foreign Application Priority Data

Aug. 4, 1989 [IT] Italy ................... 67688 A/89

[51] Int. Cl.$^5$ ............................. C12P 17/06
[52] U.S. Cl. .................... 435/125; 435/126; 435/134
[58] Field of Search ............... 435/136, 125, 126, 148, 435/189, 134

[56] References Cited

U.S. PATENT DOCUMENTS 4,946,782  8/1990  Farbood et al. ............. 435/126
4,950,607  8/1990  Cardillo et al. ............. 435/148

FOREIGN PATENT DOCUMENTS 0258993  9/1988  European Pat. Off. .......... 435/126
63-238075 10/1988  Japan.

OTHER PUBLICATIONS

*Merck Index*, Tenth Edition, pp. 265, 981 and 1293, 1983.
Arnone, A. et al., Phytochemistry 27(6) 1669–74 (1988).

*Primary Examiner*—Douglas W. Robinson
*Assistant Examiner*—S. Saucier
*Attorney, Agent, or Firm*—Dressler, Goldsmith, Shore, Sutker & Milnamow, Ltd.

[57] ABSTRACT

Process for the production of gamma- or delta-lactones according to the general formula:

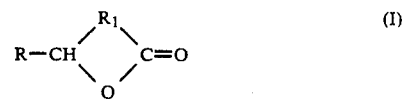

in which R is a saturated, mono-, di- or triunsaturated linear alkyl chain comprising from 2 to 10 carbon atoms and in which $R_1$ is alkylene comprising 2 or 3 carbon atoms, entailing the operation which consists in culturing, in a substrate comprising a hydroxide or hydroperoxide of linoleic acid or of linolenic acid, of their esters or of their glycerides, or of an oleic acid derivative obtained by the photooxygenation of oleic acid or autoxidation of fats which contain it, a microorganism capable of performing beta-oxidations of said substrate.

16 Claims, No Drawings

PROCESS FOR THE MICROBIOLOGICAL PRODUCTION OF GAMMA- AND DELTA-LACTONES

The present invention relates to a microbiological process for the preparation of gamma- or delta-lactones according to the general formula:

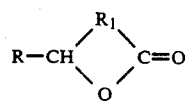

in which R is a saturated, mono-, di- or triunsaturated linear alkyl chain comprising from 2 to 10 carbon atoms and $R_1$ is alkylene comprising 2 or 3 carbon atoms.

Many lactones of the general formula (I) shown above are present in many foodstuffs, and accordingly play a very important part in the flavor industry. Such lactones are described, for example, by S. Arctander in "Perfume and Flavor Chemicals", vol. I and II, Montclair, N.J. (USA), 1969.

These substances are generally endowed with optical activity but, as emerges from recent analytical studies (see Schuring, Bioflavour 1987, P. Schreier Ed.; de Gruyter, Berlin, 1988, page 35; A. Monsandl et al., ibidem page 55), the optical purity and absolute configuration of one and the same compound can vary according to the natural source from which it has been isolated.

The compounds mentioned above are important from the industrial standpoint, but isolation of the natural sources is not practicable from an economic standpoint owing to the low concentration at which they are present in the natural state.

On the other hand, production by the microbiological degradation of advanced biosynthetic precursors is more advantageous. To this end, U.S. Pat. No. 4,560,656 describes a process for the production of (R) gamma-decanolide from natural ricinoleic acid when it is brought into contact with microorganisms belonging, for the most part, to Candida. Patent Application EP-A-258,993 describes the production of an optically active gamma-decanolide, by culturing *Sporobolomyces odorus* and *Rhodotorula glutinis* microorganisms. Other microorganisms capable of producing (R) gamma-decanolide and (R) gamma-octanolide in a culture medium comprising a vegetable oil are described in Italian Patent Application no. 67742- A/88, which constitutes a technical note only from the standpoint of Article 14, paragraph 3 of Italian patent law.

According to the present invention, cultures have been obtained of microorganisms which are capable of degrading, to the lactones according to the general formula (I) shown above, the hydroxides or hydroperoxides of natural unsaturated linear acids having either a free or an esterified carboxyl, in an optically active or racemic form.

The subject of the present invention is hence a process for the preparation of gamma- or delta-lactones according to the general formula (I), in which R and $R_1$ have the meaning defined above, entailing the operation which consists in culturing, in a substrate containing a compound selected from the group consisting of the hydroxides and hydroperoxides of linoleic acid and of linolenic acid, of their esters with $C_1$–$C_4$ lower alcohols, of their glycerides and of mixtures of such compounds, a microorganism capable of performing a beta-oxidation of said compounds.

The hydroxides and hydroperoxides of linoleic acid and of linolenic acid useful for carrying out the present invention are illustrated in Table I below, accompanied by the lactones which may be obtained as a result of their microbiological degradation.

TABLE I

HYDROXIDES AND HYDROPEROXIDES OF LINOLEIC ACID AND OF LINOLENIC ACID AND LACTONES CAPABLE OF RESULTING THEREFROM

| | DERIVATIVE | R | LACTONE |
|---|---|---|---|
| (1) | | OH | |
| (2) | " | H | " |
| (3) | | OH | |
| (4) | " | H | " |
| (5) | | OH | |
| (6) | " | H | " |

TABLE I-continued
HYDROXIDES AND HYDROPEROXIDES OF LINOLEIC
ACID AND OF LINOLENIC ACID AND LACTONES
CAPABLE OF RESULTING THEREFROM

| DERIVATIVE | R | LACTONE |
|---|---|---|
| (7) | OH | |
| (8) | H | " |
| (9) | OH | |
| (10) | H | " |
| (11) | OH | |
| (12) | H | " |
| (13) | OH | |
| (14) | H | " |
| (15) | OH | |
| (16) | H | " |
| (17) | OH | |
| (18) | H | " |
| (19) | OH | |
| (20) | " | " |

Such compounds may be used in the context of the process either in a racemic form of in an optically active form.

Such compounds may be obtained from starting materials which are readily available according to known processes. In particular, mixtures of hydroperoxides in a racemic form are obtained by the photooxygenation of linoleic acid or of linolenic acid, free or esterified with lower alcohols having 1-4 carbon atoms, or of glycerides which contain them. The photooxygenation is performed in a suitable solvent in the presence of a natural photoactivator, as described fully in the art. In this connection, reference may be made to the text "The Lipid Handbook", Chapman & Hall, London, 1986, page 453.

The hydroperoxides of the formulae (I) and (7) (Table I) are accessible in an optically active form by lipoxygenation, by means of natural lipoxygenases. In particular, the use of soybean lipoxygenases enables the hydroperoxide of the formula (7) to be obtained exclusively with the (S) configuration (H. D. Belitz & W. Grosch, Food Chemistry, Springer Verlag, 1987, pages 164–171).

In the context of the present invention, the use of hydroxides is preferred to that of the corresponding hydroperoxides. In particular, the racemic hydroxides may be obtained from mixtures of the corresponding hydroperoxides by treatment with a natural reducing agent, for example ferrous sulfate or cysteine in the appropriate solvent according to the technique described by H. D. Belitz & W. Grosch in Food Chemistry, Springer Verlag, Berlin, 1987, page 172 and H. W. Gardner, J. Agr. Food Chem., 1975, 23, 129.

The hydroxide of the formula (8) of Table I in the two enantiomeric forms, (S) and (R), is isolated from different plants, whereas the racemic form has also been isolated from natural sources.

In particular, (−)-coriolic acid is isolated from *Coriaria nepalensis* (13R) by J. H Tallent in Tetr. Letters. 1866, 4329; (+)-coriolic acid (13S) from *Mannina emerginata*, in R. C. Powel et al. in J. Org. Chem., 1967, 32, 1442; and in racemic form from absinthe essential oil, in The Lipids Handbook, Champman et al., London, 1986, 133.

The hydroxides and hydroperoxides may be subjected separately to the microorganisms in the form of free or esterified acids or of glycerides, or as a mixture of two or more products. In the first case a single lactone will be obtained, and in the others, mixtures of products.

The preferred microorganisms useable in the context of the present invention are selected for the group consisting of *Cladosporium suaveolens, Cladosproium cucumberinum, Pichia etchellsii, Sporobolomyces salmonicolor, Candida lipolytica, Fusarium poae, Phodotorula glutinis, Kloeckera saturnus, Sporobolomyces roseus, Cladosporium capsici, Pichia membranaefaciens, Pichia pamtoris, Hyphopichia burtoni, Kluyveromyces lactis, Aspergillus oryzae, Geotricum klebahnii, Saccharomyces cerevisiae, Saccharomyces delbrueckii* and *Monilinia fructicola*. These microorganisms are available from harvesting centers.

Other microorganisms capable of performing the beta-oxidation are described in U.S. Pat. No. 4,560,656 and in Patent EP-A-258,993.

According to another aspect, the invention provides a process for the preparation of a gamma- or delta-lactone according to the general formula (I) shown above, in which R is a saturated or monounsaturated linear alkyl chain comprising from 8 to 10 carbon atoms and in which $R_1$ is alkylene comprising 2 or 3 carbon atoms, entailing the operation which consists in culturing, in a substrate comprising a product selected from the group consisting of:

the product of the photooxygenation of oleic acid, of one of its esters with $C_1$–$C_4$ lower alcohols and of its glycerides, and the product of the autoxidation of fats comprising oleic acid, one of its esters with $C_1$–$C_4$ lower alcoholos and its glycerides, a microorganism capable of performing the beta-oxidation of said product.

The abovementioned products of photooxygenation and of autoxidation comprise mixtures of isomers of hydroperoxides of oleic acid containing for the most part the compound possessing a double bond at the 10-position and the hydroperoxide group at the 9-position, as well as the compound possessing a double bond at the 8-position and the hydroperoxide group at the 10-position.

The corresponding hydroxides may by obtained by reduction of the abovementioned products in the manner described above.

In particular, it is possible to obtain a good yield of gamma-dodecanolide from oleic acid derivatives.

The microorganisms useable according to this embodiment are the same as those described above.

The desired lactone is obtained from the precursors mentioned above under variable conditions of growth and in relatively short times, between 24 and 60 hours. Typically, the microorganisms are maintained in contact with the substances mentioned above at temperatures of between 20° and 30° C.

The nutrient agent in which the prior growth of the microorganisms is performed is of the conventional type. Preferably, culturing proceeds with agitation in the degradation phase which leads to the production of the lactone, whereas the production of the biomass used as a preinoculation agent may be performed either in a stationary phase or with agitation.

It has further been found that the production yield of gamma- and delta-lactons in the process according to the invention may be greatly enhanced by addition to the substrate, as defined in the present specification, of ricinoleic acid or esters thereof. It is known that several microorganisms, including those described in connection with the present invention, are able to carry out beta-oxidation of ricinoleic acid or its esters; however, the product of the beta-oxidation is the gama-decanolide which, on the other hand, is produced in a very limited amount with the use of the substrate according to this invention.

It has been found that the of ricinoleic acid or its esters to the substrate has a stimulating effect on the activity of the microorganisms which have been mentioned before, in the production of the gamma- or delta-lactons of formula (I). The addition of ricinoleic acid does not seem to have an influence on the kinetics of the microbiological process but only the activity. In other words the maximum yield is obtained within the same times which are required to achieve the maximum yield in the absence of ricinoleic acid or its esters.

Preferably, ricinoleic acid or its esters are added to the substrate in a ratio ranging from 1:2 to 2:1, and the preferred microorganisms in this embodiment are *Candida lipolitica* and *Rhodotorula glutinis*.

As is known, the lactone form of the desired compound is subject to an isomerization with the corresponding hydroxy acid form, and extraction of the lactone hence involves conversion of the hydroxy acid to the corresponding lactone.

For the extraction of the lactone, the culture broth is filtered on Celite ® which is washed with ethyl acetate, and the aqueous phase having an acid pH, preferably pH 5, is then subjected to extraction with ethyl acetate, at least twice wherever possible. The combined organic phases are extracted twice with 5% potassium carbonate solution to remove acid components. The organic phase is subsequently dried over sodium sulfate and evaporated, and the residue is distilled at 150° C. at 3 mm Hg to obtain the compound in the lactone form.

To improve the yield of lactone, it is possible to convert the corresponding acid to the lactone by bringing the pH to between 1 and 5, and preferably 1 and 3, by adding a suitable acid and heating the acidified medium to a temperature of between 50° and 110° C., and preferably between 90° and 100° C., for a period ranging from approximately 10 minutes to 2 hours depending on the temperature. The lactone may be separated from the medium by steam distillation from this acidified medium.

In the examples which follow, the quantities of lactone produced are expressed as a percentage derived from GLC analysis. Where it is indicated, the chirality of the components obtained has been determined by the method described by M. Gessner et al. in Z. Lebensm, Unter Forsch., 1988, 186, 417.

EXAMPLE 1

1 g of a mixture of hydroxylinoleic acids is subjected to cultures of Cladosoorium suaveolens. The culture broth is extracted after one day, the solvent is then removed and a crude oil containing the following is obtained:

|  | Percentage by GLC |
| --- | --- |
| gamma-5-decenolide | 5.2 |
| gamma-decanolide | 1.0 |
| delta-decanolide | 6.7 |
| gamma-6-dodecenolide | 6.3 |

EXAMPLE 2

1 g of a mixture of hydroxyoleic acids is subjected to cultures of Cladosporium suaveolens. A crude oil comprising 2.4% of gamma-dodecenolide is obtained.

EXAMPLE 3

300 g of a mixture of hydroxylinolenic acids are subjected to a culture of 300 ml of Cladosporium s. The mixture used is the product of the photooxygenation of linolenic acid reduced with $Fe^{2+}$ ions or cysteine to give a mixture of the hydroxides of formulae (10), (12), (14), (16), (18) and (20) of Table I with a ratio between the constituents of 23:13:12:14:13:25.

After 24 hours' incubation, the extract has the following composition:

| gamma-hexanolide | 0.5% |
| --- | --- |
| delta-7-decenolide | 7.2% |
| gamma-6,9-dodecadienolide | 9.0% |
| delta-octanolide | 0.9% |
| gamma-5-decenolide | 1.3% |
| gamma-5,7-decadienolide | 3.4% |

EXAMPLE 4

300 mg of a mixture of hydroxylinoleic acids are subjected to a culture of 300 ml of Cladosporium suaveolens (5 g per liter of meat extract). The mixture used, obtained by photooxygenation of linoleic acid followed by reduction, as described in Example 3, contains a mixture of the hydroxides (2), (4), (6) and (8) of Table I in a ratio of 32:17:17:32. After 24 hours' incubation, the following are obtained:

| gamma-5-decenolide | 11% |
| --- | --- |
| gamma-decanolide | 1% |
| delta-decanolide | 16% |
| gamma-6-dodecenolide | 20% |

EXAMPLE 5

An aqueous suspension, obtained in test tubes, of Cladosporium suaveolens cells is added to 17 flasks each containing 100 ml of water and 25 mg of mixture of hydroperoxides of linoleic acids, containing the compounds (1), (3), (5) and (7) in a ratio of 32:17:17:34. After 24 hours, the concentrated combined extracts give 70 mg of crude oil containing:

| gamma-5-decenolide | 0.8% |
| --- | --- |
| delta-decanolide | 2.6% |
| gamma-6-dodecenolide | 0.7% |

EXAMPLE 6

The procedure of Example 5 is repeated while adding 100 mg of a mixture of methyl esters of hydroxylinoleic acids to each flask.

After 48 hours' incubation, the combined and concentrated extracts give a crude oil containing:

| gamma-5-decenolide | 7.8% |
| --- | --- |
| delta-decanolide | 4.3% |
| gamma-6-dodecenolide | 28% |

EXAMPLE 7

100 mg of a mixture of methyl esters of hydroxylinoleic acids are added to each of 10 flasks containing 100 ml of Cladosporium suaveolens culture (direct inoculation in distilled water at pH 7).

After 7 days, the combined and concentrated extracts give a crude oil containing:

| gamma-5-decenolide | 5.1% |
| --- | --- |
| [comprising 40% of (R) isomer and 60% of (S) isomer] | |
| gamma-6-dodecenolide | 18.5% |
| [comprising 53% of (R) isomer and 47% of (S) isomer] | |
| gamma-decanolide | 1.2% |
| [comprising 7% of (R) isomer and 93% of (S) isomer] | |

EXAMPLE 8

3 flasks of 100 ml of Pichia etchelsii culture inoculated with a mixture of 300 mg of racemic hydroxides of linoleic acid are incubated for 24 hours. The extract, concentrated and distilled into an ampoule, gives 20 mg of crude oil containing:

| gamma-5-decenolide | 13% |
| --- | --- |
| gamma-decanolide | 1.3% |
| gamma-6-dodecenolide | 2.2% |

-continued

| | |
|---|---|
| gamma-decanolide [comprising 23% of (R) isomer and 77% of (S) isomer] | 22% |

EXAMPLE 9

The procedure of Example 8 is repeated using the microorganism *Fusarium poae* and, after fermentation for 24 hours, a crude oil is obtained containing:

| | |
|---|---|
| gamma-hexanolide | 0.72% |
| gamma-decanolide | 1% |
| gamma-5-decenolide [comprising 61% of (R) isomer and 39% of (S) isomer] | 2.9% |
| gamma-6-dodecenolide [comprising 20% of (R) isomer and 80% of (S) isomer] | 2.8% |

EXAMPLE 10

The procedure of Example 8 is repeated using the microorganism *Sporobolomyces salmonicolor*. 300 mg of hydroxylinoleic acids are used, separated by liquid chromatography into two fractions A and B.

After an incubation for 3 days, crude oils possessing the following concentrations are obtained:

| | Crude oil fraction A | Crude oil fraction B |
|---|---|---|
| gamma-nonanolide | 0.36% | 0.62% |
| gamma-5-decenolide | 2.4% | 0.34% |
| gamma-decanolide | 1.0% | 0.46% |
| delta-decanolide | 14.1% | 0.5% |
| gamma-6-dodecenolide | 7.12% | 0.92% |
| gamma-dodecanolide | 0.36% | — |

EXAMPLE 11

The procedure is as in Example 8, using *Candida lipolytica* and hydroxylinoleic acids separated into two chromatographic fractions A and B, and crude oils possessing the following concentration are obtained:

| | Crude oil fraction A | Crude oil fraction B |
|---|---|---|
| gamma-5-decenolide | 19.7% | 3.2% |
| delta-decanolide | 1.5% | 0.2% |
| gamma-6-dodecenolide | 0.66% | 0.2% |

EXAMPLE 12

The procedure is as in Example 8, using *Cladosporium cucumberinum* with 300 mg of hydroxylinoleic acids separated into fractions A and B, and after seven days the following are obtained:

| | Crude oil fraction A | Crude oil fraction B |
|---|---|---|
| gamma-5-decenolide | 2.6% | 0.65% |
| gamma-decanolide | 1.07% | 0.33% |
| delta-decanolide | 1.15% | 0.12% |
| gamma-6-dodecenolide | 0.7% | 0.5% |

EXAMPLE 13

2 g of sunflower oil, photooxidized in acetonitrile in the presence of a natural photoactivator (cercosporin) and then reduced (chromatographic fraction A), are introduced into 750 ml of *Cladosporium suaveolens* culture. After 48 hours, a crude oil containing the following is obtained:

| | |
|---|---|
| gamma-5-decenolide | 1.7% |
| gamma-decanolide | 0.3% |
| gamma-6-dodecenolide | 4.1% |

The fraction B of sunflower oil, photooxidized and reduced, gives under similar conditions:

| | |
|---|---|
| gamma-5-decenolide [comprising 49% of (R) isomer and 51% of (S) isomer] | 1.5% |
| gamma-decanolide | 0.3% |
| gamma-6-dodecenolide [comprising 76% of (R) isomer and 24% of (S) isomer] | 2.1% |

EXAMPLE 14

800 mg of (R)-coriolic acid [(R)-13-hydroxy-cis-9,trans-11-octadecenoic acid] are subjected to cultures of *Pichia e.* and, after 24 hours, a crude oil containing 35% of (R)-delta-decanolide is obtained.

EXAMPLE 15

800 mg of (S)-coriolic acid, obtained by lipoxygenation of linoleic acid with soybean lipoxygenases (FLUKA) according to the process described by B. Axelrod in Methods in Enxymology, 1981, page 441, and then by reduction with ferrous salts, are subjected to a culture of *Pichia etchellsii* and, after 24 hours, a crude oil containing 40% of (S)-delta-decanolide is obtained. The same compound may be produced using *Cladosporium suaveolens*.

EXAMPLE 16

The methyl esters of the acids contained in sunflower oil, obtained by transesterification with methanol in the presence of microbial lipase, were photooxidized in the presence of cercosporin, as the photodynamic substance, and sunlight by passing air through the solution in acetonitrile.

10 g of the abovementioned methyl esters in 100 ml $CH_3CH$ and 1 g cercosporin with sunlight and air are used.

At the ned of the reaction, the solution of the hydroperoxides is concentrated to a low volume and the residue is taken up with ethanol, and 3 g of the sodium slat of L-cysteine are added with strong stirring. Stirring is continued for two hours and the mixture of the methyl esters of the hydroxylated fatty acids is extracted with ethyl acetate. The resulting product is subjected to hydrolysis with lipase to give the corresponding hydroxy acids at pH 8.5 in a two-phase system consisting of methylene chloride/water. The hydroxy acids are recovered from the acidic solution by extraction and subsequent removal of the solvent.

500 mg of the hydroxy acids were inoculated into 5 flasks each containing 100 ml of a culture of *Rhodotorula glutinis* (meat extract 2 g/l).

After thirty hours' incubation at 30° C., the extract has the following composition:

| | |
|---|---|
| gamma-5-decenolide | 4.5% |
| gamma-decanolide | 1.1% |
| delta-decanolide | 9.9% |
| gamma-6-dodecenolide | 5.5% |

EXAMPLE 17

The procedure of example 16 was repeated with the use of 5 flasks each containing 100 ml of a culture of *Kloeckera saturnus*. The composition of the extract is as follows:

| | |
|---|---|
| gamma-5-decenolide | 30% |
| gamma-decanolide | 1% |
| delta-decanolide | 3% |
| gamma-6-dodecenolide | 19% |

EXAMPLE 18

The procedure of example 16 was repeated with the use of 5 flasks each containing 100 ml of culture of *Sporobolomyces roseus*. The extract has the following composition:

| | |
|---|---|
| gamma-5-decenolide | 0.8% |
| gamma-decanolide | 3.9% |
| delta-decanolide | 0.4% |
| gamma-6-dodecenolide | 3.7% |
| gamma-dodecanolide | 2.3% |

EXAMPLE 19

The procedure of example 16 was repeated with the use of 5 flasks each containing 100 ml of a culture of *Cladosporium capsici*. The extract has the following composition:

| | |
|---|---|
| gamma-5-decenolide | 1.1% |
| gamma-decanolide | 1.2% |
| delta-decanolide | 1.2% |

EXAMPLE 20

200 mg of a mixture of the product obtained by photooxygenation of grape seed oil, according to the procedure of example 16, were inoculated into 100 ml of a culture of *Kluyveromyces lactis*. After eighteen hours, the extract obtained has the following composition:

| | |
|---|---|
| gamma-5-decenolide | 0.9% |
| gamma-decanolide | 1.9% |
| gamma-6-dodecenolide | 8.9% |

EXAMPLE 21

The procedure of example 20 was applied to cultures of *Hyphopichia burtoni*. After eighteen hours, the extract has the following composition:

| | |
|---|---|
| gamma-5-decenolide | 24% |
| gamma-decanolide | 4% |
| delta-decanolide | 5% |
| gamma-6-dodecenolide | 28% |
| gamma-dodecanolide | 14% |

EXAMPLE 22

The procedure of example 20 was applied to 3 flasks each containing 100 ml of a culture of *Geotricum klebahnii*. After thirty hours, the extract has the following composition.

| | |
|---|---|
| gamma-5-decenolide | 0.9% |
| delta-decanolide | 0.8% |
| gamma-6-dodecenolide | 0.9% |
| gamma-dodecanolide | 0.1% |

EXAMPLE 23

An amount, as given in the entries in Table II, column 2, of the hydroxy acid substrate, obtained according to example 16, is mixed with an amount, as given in the entries in Table II, column 3, of ricinoleic acid. The mixtures are suspended in 100 ml water, containing 2% by weight of meat extract and 0.02% by weight of Tween. The mixtures are sterilized and incubated with the cultures of *Candida lipolytica*. obtained from a slant with distilled water or from a preinoculum. The cultures are stirred at 27°-30° C. for the time given in Table I. At the given time, the fermentation is stopped by bringing the pH to 2 and solvent extraction is carried out with addition of an internal standard (gamma C11). The solvent is evaporated off and the residue is distilled at 100°-120° C. under a vacuum of about 0.1-0.3 mmHg. The resulting product containing the desired lactone is weighed and analyzed. The results obtained with different ratios of the substrate and ricinoleic acid and different times are given in Table II.

EXAMPLE 14

The procedure of example 23 is followed with the use of *Rhodotorula glutinis*.

The results are given in Table III.

TABLE II

| t(n) | Substrate ml/100 ml | Ricinoleic acid ml/100 ml | $\gamma C_{10}\Delta 5$ mg/100 ml | $\delta C_{10}$ mg/100 ml | $\gamma C_{12}\Delta 6$ mg/100 ml | $\gamma C_{12}$ mg/100 ml | 1 + 2 + 3 + 4 mg/100 ml |
|---|---|---|---|---|---|---|---|
| 15 | 4 | 1 | 42 | 6.5 | 23.5 | 15 | 87 |
| 15 | 4 | 2 | 60 | 8 | 28.5 | 22 | 118.5 |
| 24 | 4 | 0 | 61.5 | 15.5 | 55 | 38 | 194 |
| 24 | 4 | 2 | 85.5 | 9.5 | 85 | 57 | 231 |
| 24 | 4 | 4 | 136.5 | 8 | 68 | 41 | 254 |
| 30 | 4 | 0 | 85 | 1.5 | 81 | 35 | 175 |
| 30 | 4 | 4 | 132.5 | — | 62 | 26 | 220 |
| 30 | 4 | 8 | 118.5 | 7 | 191 | 95.5 | 412 |

The amounts of the substrate and ricinoleic acid are given as ml/100 ml of the culture and the amounts of the lactone as mg/100 ml of the culture.

γC₁₀Δ5 = gamma-5-decenolide
δC₁₀ = delta decanolide
γC₁₂Δ6 = gamma-6-dodecenolide
γC₁₂ = gamma-dodecanolide

TABLE III

| t(n) | Substrate ml/100 ml | Ricinoleic acid ml/100 ml | γC₁₀Δ5 mg/100 ml | δC₁₀ mg/100 ml | γC₁₂Δ6 mg/100 ml | γC₁₂ mg/100 ml | 1 + 2 + 3 + 4 mg/100 ml |
|---|---|---|---|---|---|---|---|
| 12 | 4 | — | 15.5 | — | 9 | 7 | 31.5 |
| 12 | 4 | 8 | 30 | 0.25 | 38 | 32.5 | 101 |
| 48 | 4 | — | 2.1 | — | 2.7 | — | 5 |
| 48 | 4 | 8 | 12 | — | 9.5 | 7 | 28.5 |
| 48 | 8 | 4 | 27 | — | 18 | 18.5 | 63.5 |
| 55 | 8 | 8 | 1.5 | — | 103 | 45 | 149.5 |
| 144 | 8 | 4 | 110 | — | 64 | 53.5 | 227.5 |
| 144 | 8 | 4 | 135 | — | 146 | 48.5 | 329.5 |

The process according to the invention hence provides the possibility of obtaining industrially useful compounds from inexpensive sources derived from fats which have no other nutritional value. As emerges from the examples involving the microorganisms examined, the process of degradation of the hydroxide or hydroperoxide in the optically active form is enantioselective, as a result of which it is possible to produce the desired lactone with a high enantiomeric purity.

We claim:

1. A process for the preparation of a gamma- or a delta-lactone according to the general formula:

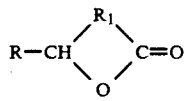 (I)

in which R is a saturated, mono-, di- or tri-unsaturated linear alkyl chain comprising from 2 to 10 carbon atoms and R₁ is an alkylene group having 2 or 3 carbon atoms, said lactone being selected from the group consisting of delta 6,9-γ-dodecendienolide, delta 5,7-γ-decadienolide, delta 7-δ-decenolide, delta 6-δ-octenolide, γ-hexanolide, delta 6,8 tetradeca-δ-dienolide, delta 6-γ-dodecenolide, delta 5-γ-decenolide, δ-decanolide and delta 6,8,11-tetradeca-δ-trienolide, comprising the steps of:

a) purposely oxidizing by a oxidation process selected for the group consisting of autooxidation, photooxidation and lipoxygenation, a substrate comprising a compound selected from the group consisting of linoleic acid linolenic acid, C₁-C₄ alkyl esters of linoleic acid, C₁-C₄ alkyl esters of linolenic acid, a glyceride of linoleic acid, a glyceride of linolenic acid and mixtures thereof, thereby to obtain the corresponding hydroperoxy- and/or hydroxy-derivatives and mixtures thereof, b) reducing the reaction product of step a) by means of a reducing medium thereby to convert said hydroperoxide derivative to the corresponding hydroxy- derivative, and c) culturing in a medium comprising the reaction product of step b) a microorganism capable of performing beta-oxidation thereby to produce at least one of said lactones and recovering said at least one lactone from the culture medium.

2. The process of claim 1, wherein the oxidation process in step a) is photooxygenation.

3. The process of claim 1, wherein said substrate is a fat comprising linoleic or linolenic acid and the oxidation process of step a) is autooxidation.

4. The process of claim 1, wherein the oxidation process in step a) is lipoxygenation carried out by means of lipoxygenase.

5. A process according to claim 1, wherein said reducing agent is selected from the group consisting of ferrous sulphate and cysteine.

6. A process for the preparation of a gamma- or delta-lactone according to the general formula:

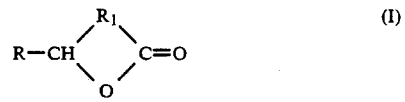 (I)

in which R is a saturated or mono unsaturated linear alkyl chain having from 8 to 10 carbon atoms and in which R₁ is an alkylene group having 2 or 3 carbon atoms comprising the steps of:

a) purposely oxidising by an oxidation process selected from the group consisting of photooxygenation and autooxidation a substrate comprising a compound selected from the group consisting of oleic acid, C₁-C₄ alkyl esters f oleic acid, a glyceride of oleic acid and mixtures thereof, thereby to obtain the corresponding hydroperoxy- and hydroxy- derivatives and mixtures thereof, b) reducing the reaction product of step a) by means of a reducing medium, thereby to convert said hydroperoxide derivative to the corresponding hydroxy-derivative, and c) culturing in a medium comprising the reaction product of step b) with a microorganism capable of performing beta-oxidation of said reaction product, thereby to produce at least one of said lactones of formula (I) and recovering said at least one lactone from the reaction medium.

7. The process of claim 6, wherein said reducing agent is selected from the group consisting of ferrous sulphate and cysteine.

8. The process of claim 1 for the preparation of (S)-delta-decanolide, wherein the reaction product of step (a) comprises (S)-13-hydroxy (or hydroperoxy) -cis-9, trans-11-octadecadienoic acid and wherein the microorganism employed is selected from the group consisting of *Pichia etchellsii* and *Cladosporium suaveolens*.

9. The process of claim 8 wherein said (S)-13-hydroxy (or hydroperoxy) cis-9, trans-11-octadecadienoic acid is obtained by lipoxygenation of linoleic acid with one or more soybean lipoxygenases.

10. The process according to claim 1 or 6, wherein said hydroxy- or hydroperoxy- derivative is in an optically active form.

11. The process according to claim 1 or 6, wherein ricinoleic acid or an ester thereof is added to the culture medium in step c).

12. The process of claim 11, wherein the ratio between the reaction product of step b) and added ricinoleic acid or ester thereof in the culture medium is in the range from 1:2 to 2:1.

13. The process of claim 11, wherein the microorganism is selected from the group consisting of *Candida lipolytica* and *Phodotorula glutinis*.

14. A process for the preparation of a gamma- or a delta-lactone according to the general formula:

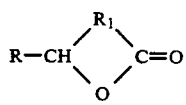

in which R is a saturated, mono-, di or tri-unsaturated linear alkyl chain comprising from 2 to 10 carbon atoms and $R_1$ is an alkylene group having 2 or 3 carbon atoms, said lactone being selected from the group consisting of delta 6,9-γ-dodecendienolide, delta 5,7-γ-decadienolide, delta 7-δ-decenolide, delta 6-δ-octenolide, γ-hexanolide, delta 6,8 tetradeca-δ-dienolide, delta 6-γ-dodecenolide, delta 5-γ-decenolide, δ-decanolide and delta 6,8,11-tetradeca-δ-trienolide, comprising culturing, in a medium a substrate consisting essentially of one or more compounds of the group consisting of the hydroxides and hydroperoxides of linoleic acid and of linolenic acid, their esters with $C_1$-$C_4$ lower alcohols, and mixtures thereof, a microorganism capable of performing a beta-oxidation of said compounds and recovering at least one lactone of the formula I from the culturing medium.

15. A process for the preparation of a gamma- or a delta-lactone according to the general formula:

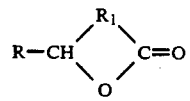

in which R is a saturated, mono-, di or tri-unsaturated linear alkyl chain comprising from 2 to 10 carbon atoms and $R_1$ is an alkylene group having 2 or 3 carbon atoms, said lactone being selected from the group consisting of delta 6,9-γ-dodecendienolide, delta 5,7-γ-decadienolide, delta 7-δ-decenolide, delta 6-δ-octenolide, γ-hexanolide, delta 6,8 tetradeca-δ-dienolide, delta 6-γ-dodecenolide, delta 5-γ-decenolide, δ-decanolide and delta 6,8,11-tetradeca-δ-trienolide, comprising the steps of:
  a) subjecting a substrate comprising a compound selected from the group consisting of oleic acid, $C_1$-$C_4$ alkyl esters of oleic acid, a glyceride of oleic acid and mixtures thereof, to photooxidation or lipoxygenation conditions which induce the formation of the corresponding hydroperoxy- and hydroxy- derivatives and mixtures thereof and b) culturing in a medium comprising the reaction product of step a) with a microorganism capable f performing beta-oxidation of said reaction product, thereby to produce at least one of said lactones of formula (I) and recovering said at least one lactone from the culture medium.

16. The process as claimed in one of claim 7, 9, 12, 14, 15, in which said microorganism is selected from the group consisting of *Cladosporium suaveolens, Cladosporium cucumberinum, Pichia etchellsii, Sporobolomyces salmonicolor, Candida lipolytica, Fusarium poae, Rhodotorula glutinis, Kloeckera saturnus, Sporobolomyces roseus, Cladosporium capsici, Pichi membranaefaciens, Pichia pamtoris, Hyphopichia burtoni, Kluyveromyces lactis, Aspergillus oryzae, Geotricum klebahnii, Saccharomyces cerevisiae, Saccharomyces delbrueckii* and *Monilinia fructicola*.

* * * * *